United States Patent
Bohn et al.

(10) Patent No.: US 9,157,836 B2
(45) Date of Patent: Oct. 13, 2015

(54) METHOD AND DEVICE FOR REMOVING A SAMPLE FROM A COIL

(75) Inventors: Andreas Bohn, Hilchenbach (DE);
Klaus Baeumer, Kreuztal (DE);
Thomas Runkel, Siegen (DE)

(73) Assignee: SMS GROUP GMBH, Duesseldorf (DE)

( * ) Notice: Subject to any disclaimer, the term of this patent is extended or adjusted under 35 U.S.C. 154(b) by 1 day.

(21) Appl. No.: 13/985,605

(22) PCT Filed: Feb. 2, 2012

(86) PCT No.: PCT/EP2012/051744
§ 371 (c)(1),
(2), (4) Date: Aug. 15, 2013

(87) PCT Pub. No.: WO2012/113631
PCT Pub. Date: Aug. 30, 2012

(65) Prior Publication Data
US 2013/0312544 A1    Nov. 28, 2013

(30) Foreign Application Priority Data

Feb. 23, 2011 (DE) .......................... 10 2011 012 192
Apr. 1, 2011 (DE) .......................... 10 2011 015 896
Jun. 14, 2011 (DE) .......................... 10 2011 077 461

(51) Int. Cl.
*G01N 1/04* (2006.01)
*B21C 47/18* (2006.01)
(Continued)

(52) U.S. Cl.
CPC *G01N 1/04* (2013.01); *B21C 47/18* (2013.01); *B21C 47/326* (2013.01); *B21C 51/00* (2013.01)

(58) Field of Classification Search
CPC ........ B23D 31/00; B23D 33/02; B21C 47/18; B21C 47/326; B21C 51/00; B21C 47/00; B21C 47/24; B21C 47/34; B21C 47/3433; G01N 1/04; B26D 1/605; Y10S 83/919
USPC ........ 73/864, 864.41; 83/649, 919; 242/56 R; 266/48
See application file for complete search history.

(56) References Cited

U.S. PATENT DOCUMENTS 3,375,743 A * 4/1968 Levy .................................. 83/27
3,531,058 A * 9/1970 Birschkus ..................... 242/520
(Continued)

FOREIGN PATENT DOCUMENTS

DE    28 15 969    10/1978
DE    29 24 379    1/1981
(Continued)

*Primary Examiner* — Daniel S Larkin
*Assistant Examiner* — Jamar Ray
(74) *Attorney, Agent, or Firm* — Abelman, Frayne & Schwab

(57) ABSTRACT

The present invention relates to a device (1) for removing a sample (24) from a coil (2), comprising at least one bottom roll unit (30, 32) for supporting the coil (2) during removal of the samples, at least one contact roll unit (40, 42) pressable against an outer surface of the coil (2), and at least one strip binding device for binding the coil (2) supported on the at least one bottom roll unit (30, 32). The present invention further relates to a device for removing a sample (24) from a coil (2), comprising a deflection device (70) for deflecting a material beginning (20) of the coil (2) from a beneath located layer (22), wherein the deflection device is so formed that the strip beginning only elastically deflected from the beneath layer (22). The invention also relates to corresponding methods.

12 Claims, 4 Drawing Sheets

(51) Int. Cl.
*B21C 47/32* (2006.01)
*B21C 51/00* (2006.01)

(56) References Cited

U.S. PATENT DOCUMENTS

| | | |
|---|---|---|
| 4,344,605 A | 8/1982 | Ganseuer |
| 4,399,729 A * | 8/1983 | Malinowski et al. ........... 83/455 |
| 4,549,700 A | 10/1985 | Ganseuer |
| 7,401,485 B2 * | 7/2008 | Peter et al. ..................... 72/148 |
| 2008/0190258 A1 | 8/2008 | Moser |
| 2012/0187091 A1 * | 7/2012 | Grzyb et al. ................. 219/69.1 |

FOREIGN PATENT DOCUMENTS

| | | |
|---|---|---|
| DE | 44 11 905 | 11/1994 |
| DE | 199 08 076 | 9/2000 |
| DE | 10 2007 017 383 | 8/2008 |
| EP | 44 923 A2 | 2/1982 |
| EP | 102 940 A2 | 3/1984 |
| EP | 0 497 182 A1 | 8/1992 |
| EP | 497 182 A1 | 8/1992 |
| EP | 188 284 | 5/2009 |
| GB | 2 068 796 | 8/1981 |
| JP | 08 26 7134 | 10/1996 |
| JP | 2010 253 338 | 11/2010 |
| WO | 2009 047395 | 4/2009 |

* cited by examiner

METHOD AND DEVICE FOR REMOVING A SAMPLE FROM A COIL

TECHNICAL FIELD

The present invention relates to device and method for removing a sample from a coil, in particular a metal strip coil.

STATE OF THE ART

In a rolling mill, usually during production of rolled metal strips, those are wound in a coil, also called a reel, after conclusion of a rolling process. Correspondingly, a coil contains a long uncut section of a rolled metal strip. A metal strip coil typically has a weight up to 40 ton so that for a reliable handling of the coil, correspondingly massive devices are required.

In order to check the production quality of respective rolled strips and to be able to insure it, it is necessary to remove a sample from a respective coil. Typically, samples are removed from a strip beginning that lies on the outer surface of the coil. In particular, a piece of the strip beginning and/or strip end is separated to obtain a sample of the material wound in a coil. The samples then are fed to separate test means.

Advantageously, in addition to an actual sample removal, trimming of the strip beginning and/or the strip end is achieved.

The respective coil is so held together with a band that it does not spring up during transportation after leaving a corresponding winding device or a coiler but rather retains its original wound shape. Such a band is usually formed as a steel band or as a bent flat steel material in order to be able to withstand forces acting during transportation.

In order to be able to take a sample of a such binded coil, the strip binding material should be separated, a strip beginning unwound from the coil, a piece of the unwound strip beginning be separated as a sample, the strip beginning be again rewound on the coil, and a new band be brought around the coil in order to prevent the springing-up of the coil during a further renewed transportation.

In order to be able to effect a new binding of the coil, the coil is either bound manually, which is expensive, or is transported to a separate binding station after a sample has be removed. During unwinding of a coil, the strip beginning is plastically deformed, at least at corresponding material and material thickness, in order to obtain an advantageous separation position. During a following rewinding of the strip beginning, the strip again is plastically bent in a coil shape.

With respect to sample removal, EP1888284B1 discloses an apparatus and a method for cropping ends of or for separating sample pieces of rolled strip wound into a coil and having shears, first and second bottom rolls, and at least one position-adjustable contact roll.

DE102007017383A1 discloses an apparatus for binding coils and in which the coil is supported on a rotatably driven mandrel, and a bending station is provided that feeds a pre-bent flat steel band having a length corresponding to a coil circumference to the coil. This flat steel band is wound around the coil with at least one contact roll, and the ends of the flat steel band are connected with each other.

The state of the art further discloses bending off a strip beginning from a coil for removing a sample and so deflecting the strip beginning that it is fed to a cutting device. Such an apparatus is disclosed, e.g., in WO 2009/047395A1.

The so plastically deformed strip beginning should subsequently be rewound on the coil.

DESCRIPTION OF THE INVENTION

Correspondingly, the object of the invention is a device and a method for an efficient removal of a sample from a coil.

Correspondingly, a device for removing a sample from a coil comprises at least one bottom roll unit for supporting the coil during removal of the sample, at least one contact roll unit pressable against an outer surface of the coil, and at least one strip binding device for binding the coil supported on the at least one bottom roll unit. With a contact roll unit, it can be achieved that the coil does not spring up during sample removal and subsequent binding. In this way, safety of the operating persons is increased, and the sale quality of the coil is improved. The coil which s held by the contact roll unit and which, correspondingly does not sprig up after removal of a sample, can then be directly provided with a band by the strip binding unit after the removal of a sample. Correspondingly, an expensive manual binding or transfer to a separate binding station can be eliminated, and the coil becomes sale-ready immediately after the removal of a sample and binding.

In other words, with the inventive device, an efficient sample removal and a resulting product quality are achieved. This is because the opening of the coil, i.e., band removal, removal of the sample, and the following closing of the coil can be carried out within a single device. The springing up of the coil during the removal of the sample can be prevented with a contact roll unit. Thus, the removal of the sample does not influence the winding quality of the coil.

In order to be able to achieve an efficient binding of the coil after the removal of the sample, rolls of the bottom roll unit and/or rolls of the contact roll unit have recesses for displacing therethrough of a strip binding material and/or for forming binding channel.

Alternatively or in addition to the above-mentioned recesses, rolls of the bottom roll unit and/or rolls of the contact roll unit have, respectively, at least two roll units so that a strip binding material is displaceable between separate roll elements and/or a strip binding channel is formed therebetween.

A reliable handling of the coil is achieved by providing at least one second contact roll unit which is pressable against the out surface of the coil. Advantageously, there are also provided at least one stationary bottom roll unit and at least one displaceable bottom roll unit for adapting the device to different coil diameters. Advantageously, the respective bottom roll units and the respective contact roll units are offset relative to each other by 90° to reliably secure the coil from all directions.

Advantageously, there is provided a sample removing device for removing a sample from a strip beginning of the coil.

Advantageously, there is provided at least one deflection device for deflecting a strip beginning of the coil from a beneath located layer, wherein the deflection device is so formed that the strip beginning only elastically deflected from the beneath located layer. In this way, it is achieved that plastic deformation during the sample removal, which necessitates a new plastic deformation during rewinding of the strip beginning, is prevented.

Correspondingly, the device for removing a sample from a coil comprises a deflection device for deflecting a material beginning of the coil from a beneath located layer (22). The deflection device is so formed that the strip beginning only elastically deflected from the beneath located winding.

Here, it is understood that plastic deformation of the metal strip unwound from the coil should not take place. Thereby, it is achieved that the strip beginning completely lies on the beneath located layer again after a sample has been removed, without any further deformation steps being necessary.

Advantageously, the deflection device has a deflection element that has a geometry, alignment, and/or setting such that the strip beginning of the coil is so deflected with a force from the beneath located layer that simply an elastic deformation of the strip beginning takes place. Advantageously, the deflection element is formed as a wedge, preferably with an acute angle.

In order to achieve a corresponding elastic deflection, the deflection device is advanced to an outer surface of the coil substantially tangentially.

For removal of a sample, a separation device for separating a sample from the coil can be provided. The separation device preferably acts on the strip beginning transverse to the beneath located layer of the coil. In this way, a plastic deformation of the strip for removal of a sample can be prevented. In particular, the separation device comprises shears, anvil, or knife bar with which the separation of a sample can be carried out without damaging of the beneath located layer of the coil.

In order to enable an efficient treatment of a coil, advantageously a strip binding device for binding the coil is provided, so that the coil after rewinding of the strip beginning need not be displaced for a following binding.

There are further provided direct of indirect measuring sensors, e.g., in form of a sensor for following the leading strip edge or in form of a sensor for monitoring the coil rotation with respect to the position of the deflection device in order to control and monitor removal of the sample, desired small deflection of the strip beginning from the beneath located layer of the coil.

Correspondingly, a method of removing a sample from a coil comprises the steps of: positioning the coil on at least one bottom roll unit, pressing at least one contact roll unit against an outer surface of the coil, removing a sample, binding the coil supported on the at least one bottom roll unit with a binding device.

The method comprises alternatively or in addition the steps of: deflecting a strip beginning of the coil from a beneath located winding so that only elastic deformation of the strip beginning takes place, removing a sample from the elastically deflected strip beginning of the coil, and placing the strip beginning on the beneath located layer.

The maximum force which is to be used for providing only an elastic deformation is calculated based on obtained test data and/or based on determined empirical data.

BRIEF DESCRIPTION OF THE DRAWINGS

Advantageous further embodiments and aspects of the present invention will be explained in detail by the following description of the drawings. The drawings show.

DETAILED DESCRIPTION OF THE PREFERRED EMBODIMENT

Figure 1:
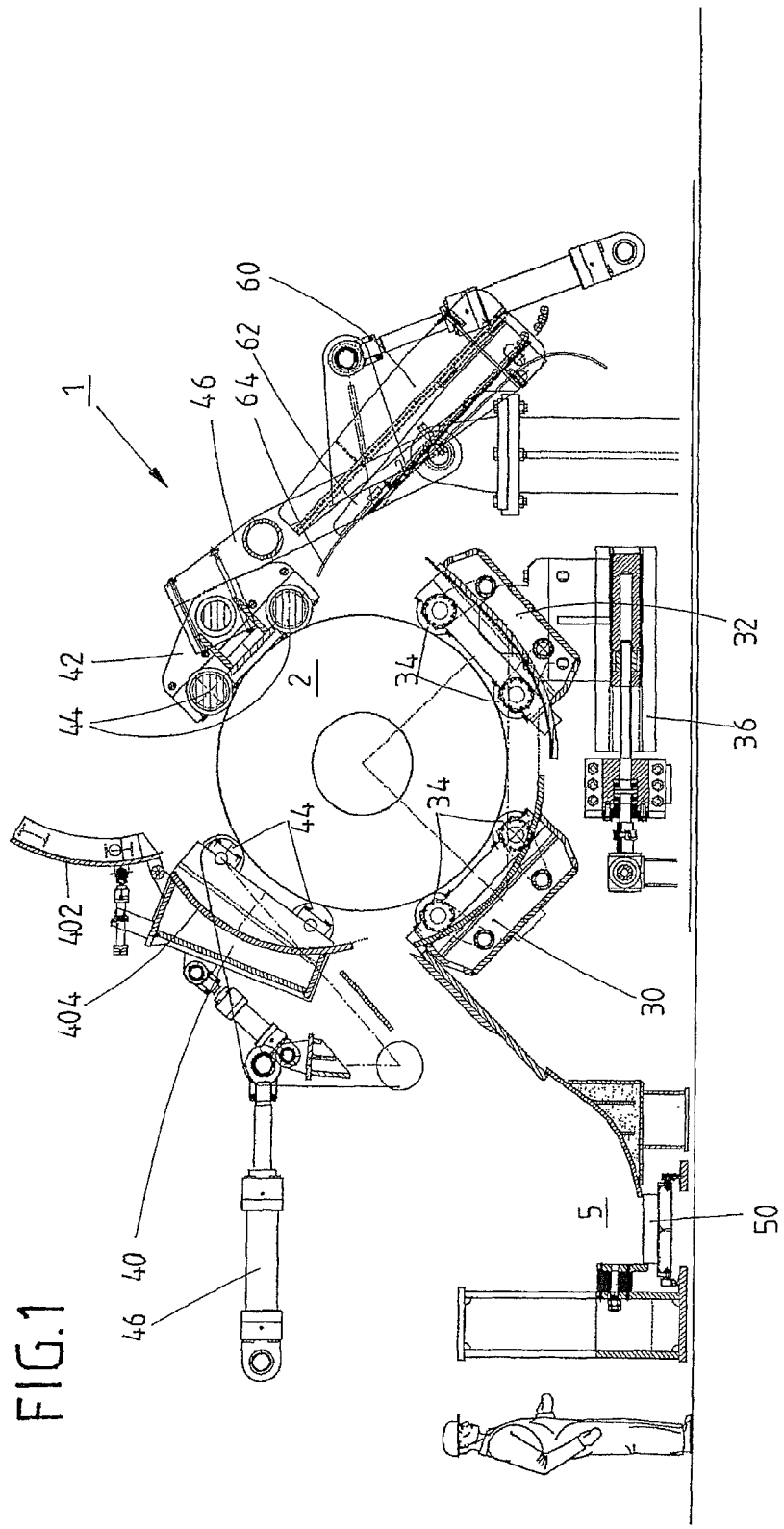
FIG. 1 a schematic side view of a device for removing samples from a coil according to the present invention.

Below, the preferred embodiments of the invention will be described with reference to the drawings.

In this connection, the same or similar elements are designated with the same reference numerals, and a repeated description of these elements will be particularly avoided in order to prevent redundancy.

FIG. 1 shows a device 1 for removing samples of a coil 2, in particular, of a metal strip coil. For taking samples of a coil, it is necessary to loose the original binding of the coil so that a strip beginning of the coil can be pulled off the coil and then a section of the strip beginning be separated as a sample. After separation of the sample from the strip beginning, the new strip beginning must be again be placed against the coil, i.e., be wound again, and then must be bound anew.

FIG. 1 shows a coil 2 which is supported on two bottom roll units 30 and 32. The bottom roll units include, respectively, rolls 34 which directly contact, respectively, the outmost winding of the coil 2, i.e., the outer surface of the coil 2, and which rotatably support the coil 2 for rotation about its winding axis.

One bottom roll unit 30 is stationary and the second roll unit 32 is adjustable with a displacement device 36 in order to be able to receive, without any problem coils having different diameters. With the movable bottom roll unit 32, therefore, geometrical relationships within the device 1 can be identically established to the most possible extent in accordance with the respective diameter of the coil.

There are provided a first contact roll device 40 and a second contact roll device 42 which are offset with respect to the bottom roll units 30, 32 by about 90° relative to the coil 2. The contact roll devices have likewise two rolls 44, respectively, which directly contact the outer winding of the coil 2. The contact devices 40, 42 can be put against the out winding of the coil 2, by respective displacement devices 46, which can be formed, e.g., by a hydraulic cylinder, dependent on the diameter of the coil 2, and can be completely lifted off the coil to enable a simple release and lifting the coil upwardly.

The contact devices 40, 42 serve for holding or fixing the coil windings when the binding of the coil is loose in order to be able to take a sample. In this way, jumping up of the coil 2 and loosening of the windings can be prevented.

The bottom roll units 30, 32 and the contact roll units 40, 42 are preferably, arranged equidistantly or at the same rotationally angle about the coil 2 in order to provide a uniform pressure on separate coil windings and, in particular on the outmost winding during pulling-off the strip beginning for removing a sample.

For actually removing the sample from coil 2, the strip beginning is pulled from the coil 2 in the direction of a sample removing station 5 and there is separated by a separation device, not shown in FIG. 1, wherein the separated sample is transported to a corresponding analyzing station with a sample feeding device 50.

After a sample is taken, the strip end is again advanced to the coil 2, e.g., by rotating the coil in a direction opposite the unwinding direction, and the coil is again bound by a binding device 60. The strip binding device 60 includes a gate from which a strip binding material 64, in particular a flat steel band is led out and then guided around the coil 2.

Figure 2:
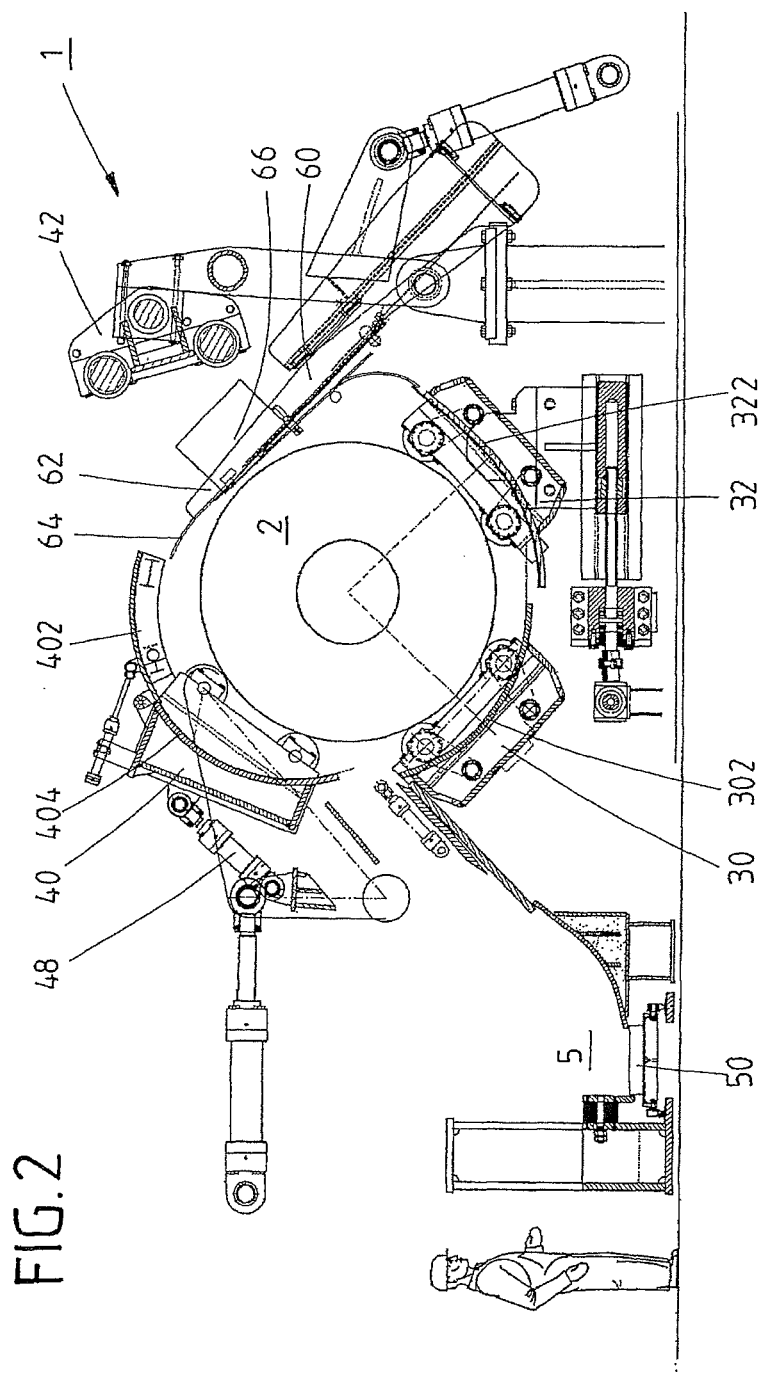
FIG. 2 the device according to FIG. 1 in a second operational condition.

This condition is shown in FIG. 2. In FIG. 2, one of the contact roll devices 42 is lifted off the coil 2 and is pivoted out of the way. The strip binding device 60 provides, at gate 62, the strip binding material, in particular a flat steel band. This flat steel band is guided around the coil 2 by means of guide devices 402, 404 provided on the contact roll unit 40. Other guide devices are provided on the bottom roll units 30, 32 in form of guide devices 302 and/or 322. In other words, the binding material 64 that is led out of the gate 62, can be once guided about the coil when it is guided in respective guide devices 402, 404, 302, 322, and then again be advanced to the strip binding device 60.

At the strip connection device 66, both ends of the strip binding material 64 are fixedly connected with each other, so that the coil 2 retains its closed shape when the contact roll device is also lifted off the coil 2.

In the shown embodiment, the guide device 402 is pivotable relative to the second portion of the guide device 404, wherein both are provided on the contact roll device 40. In other words, firstly, the guide device 402 is pivoted in the guide path of the strip binding material 64 when actually the strip should be bound.

The selected rolls 34 of the bottom roll units 30, 32 and the selected rolls of the contact roll devices 40, 42, namely, the rolls 44, are advantageously formed as driven rolls. All of the rolls 34, 44 can be driven. By driving the rolls 34, 44, the rotation of the coil 2 on the bottom roll devices 30, 32 becomes possible which enables an actual removal of a sample, on one hand. On the other hand, the driving serves for bringing the coil 2, after removal of the sample, again in a closed form. The rolls drive the coil over its outer surface.

Further, it is possible by driving respective rolls 34, 44, to apply a certain pull to the outmost winding of the coil in such a way that the outmost coil tightly lays on a respective below-located layer of the coil.

The strip binding material can be guided around the coil 2 particularly easy when the respective rolls 34, 44 either provided with recesses for guiding through the strip binding materials 64 or the rolls 34, 44 are divided, being formed of arranged next to each other roll elements.

In the view shown in FIG. 2, a schematic view is shown in such a way that the guide devices 402, 404, 302, 322 are located between respective roll elements of the rolls 34, 44. Correspondingly, the binding can be effected directly after taking the sample or directly after rewinding the strip beginning, without the respective rolls 34, 44 being in the path during renewed binding of the coil.

The strip binding device 60 can be pivoted onto the coil or toward the vicinity of the coil 2 after the second contact roll devices 42 is lifted off the coil and is pivoted into a park position.

In an alternative embodiment, it is, however, also possible to integrate the strip binding device 60 with the second contact roll device 42 so that the pivoting step can be eliminated, whereby the efficiency of the sample removal can be further increased.

FIG. 2 shows that during the binding, the coil 2 is held at least by the bottom roll units 30, 32 and the contact roll unit 40 and, in particular, the outmost winding and the strip beginning from which a sample is taken, is reliably and fixedly held by the contact roll unit 40. In this way, it is insured that the outmost windings and particularly the outer winding of the coil tightly lays on the beneath located windings, whereby the sale quality of the newly bound coil is correspondingly improved, and binding of the coil can take place at the same station after the sample is removed, without the need in moving the coil 2, with the connected therewith hazards.

After pivoting in of the strip binding device 60 and pivoting out of the second contact roll unit 42, the guide devices 402, 404, 302, 322 form a complete binding band channel or the channel for guiding the strip binding material 64, so that the strip binding material 64 can be completely guided around the coil and can correspondingly bind the coil.

The possibility of positioning of the movable bottom roll unit 22 by the displacement device enables to better position the coil 2 from a group of coils, having difficult diameters, taking into account a respective strip beginning from which a sample of the coil should be removed.

The contact roll unit 40 is pivoted with an adjusting device 48 in order to be able to guide the strip beginning in accordance with the sample removal and to be able to press the strip beginning again against the coil 2 after the removal of the sample. It is possible to so pivot the contact roll unit 40 about a pivot point that both rolls 44 can either be arranged so that they follow the actual outer surface of the coil 2, with the other rolls 44, 34 of both bottom roll units 30, 32 and of the second contact roll unit 42, essentially along a circular path, or so that one of the two shown rolls 44 of the contact roll unit 40 can deviate from the imaginary circular path and be so deflected that the strip end, from which a sample should be removed, is guided by the deviated roll. During rewinding of the coil after removal of the sample, the deviated roll serves to guide the strip end again toward the coil 2 and place it onto the outermost winding located below. This can be effected by pivoting the roll 44 again into the imaginary circular path.

The position of the strip end during the entire time the probe removal takes place can be monitored by direct or indirect sensors. Under direct sensors, the sensors which actually measure the strip, e.g., by using imaging methods, e.g., using a camera, scanning with photoelectrical sensor, or similar methods, are understood. An indirect monitoring of the strip beginning can be achieved by measuring respective revolutions of the coil 2 or by measuring the rotation of respective rolls 34, 44 which directly contact the outer surface of the coil 2.

The here described device and method for removal a sample is particularly suitable for removal of samples of thick strip coils with a high tensile strength.

The coils which are form of high-strength strips have a tendency of springing up upon opening which holds a high danger of injury, and makes more difficult a following rewinding of the coil without intermediate spaces. However, when the coil 2 is guided on both bottom roll devices 30, 32 and both contact roll devices 40, 42 after rotating the coil 2, the coil cannot spring up after opening of the binding so that the coil 2 can be unwound without danger.

Figure 3:
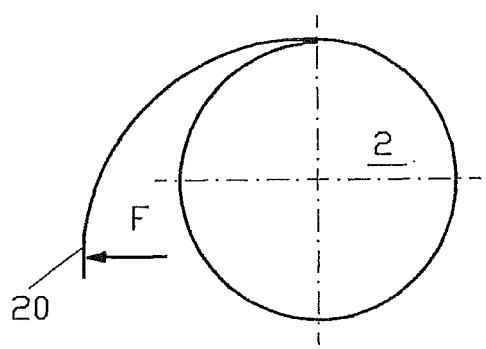
FIG. 3 a schematic view illustrating deflection of a strip beginning from a coil with remaining plastic deformation.
Figure 4:
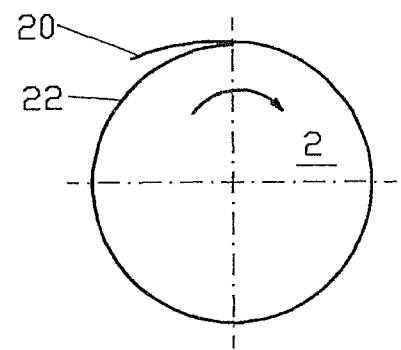
FIG. 4 a schematic view illustrating the plastic deformation that remained after a new strip beginning was placed against the coil.

FIGS. 3 and 4 schematically show behavior of the strip beginning 20 of a coil 2 which is deflected with a force F for removing a sample that causes a remaining plastic deformation in the coil material. FIG. 3 schematically shows a condition in which the strip beginning 20 is deflected with a force F to enable removal of a sample. FIG. 4 shows a condition in which the strip beginning 20 is again wound on the coil 2. As a result of the still remaining plastic deformation of the strip beginning 20, the strip beginning 20 does not directly and completely lay on the below located layer 22.

However, it is this method that has been used up to now, namely, to so deflect the strip beginning 20 under application of a corresponding force that it moves in a sample removal area for separating the sample.

Figure 5:
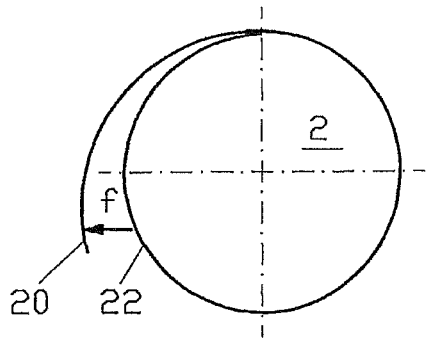
FIG. 5 a schematic view illustrating deflection of a strip beginning with a simple elastic deformation.
Figure 6:
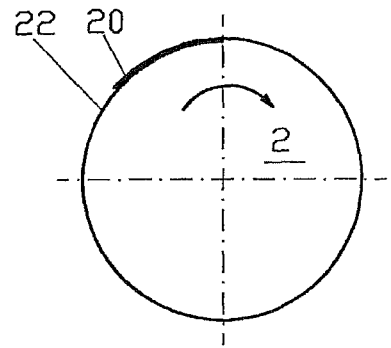
FIG. 6 a schematic view illustrating placing a new strip beginning after an elastic deformation.

Proceeding therefrom, the inventive approach for separating a sample from a coil 2 according to subject matter of the present invention is shown in FIGS. 5 and 6. FIG. 5 shoes use of force f for deflecting the strip beginning 20 from a below located layer 22 of the coil in such a way that only an elastic deformation of the material takes place, without any remaining plastic deformation. Correspondingly, during rewinding of the new spring beginning 20 onto the beneath located layer 22 of the coil 2 after removal of the sample, a condition shown in FIG. 6 is produced, namely, the material and, in particular, the strip beginning 20 is so bounces back that the strip beginning 20 directly and completely lays on the below located layer 22 of the coil 2. Correspondingly, no plastic deformation is produced in the strip beginning 20, so that the material quality can be maintained with the method shown in FIGS. 5 and 6.

The force that leads to an elastic deformation of the strip beginning 20 and not to a remaining plastic deformation, can either be calculated based on empirical data or experimentally for a respective material and strip strength.

The separation of the material from coil 2 can lead, in addition to removal of a sample, to formation of another profile of the strip beginning 20 after the coil is formed, e.g., to a more sharp separation edge.

Since long ago, different separation method, e.g., mechanical or thermal cutting, are known for separating material from a wound coil which are used in carrying out the process shown in FIGS. 3 and 4. With this, for use of a separation device, the strip beginning 20 should be deflected from the coil under a plastic deformation in order to provide, when using a mechanical cutting method, a necessary additional space between the coil and the deflected strip beginning or when using a thermal cutting method, the necessary space therebetween which is necessary for protection of the outer windings of the coil from damages.

With machining separation of the material, the material need not principally be lifted, however, the problem with this method consists in that the material is either not completely separated and, correspondingly, must be subsequently teared off, with resulting onerous ridges or, with a complete separation, there is a danger that the located below coil winding or at least its outer surface becomes damaged.

The spacing of the strip beginning 20 from the beneath located layer 22, such as shown in FIG. 4, is not desirable because this strip beginning 20 can be placed again onto the coil or the located beneath layer 22 only with additional expenses. The spaced strip beginning 20 is disadvantageous during a subsequent treatment, e.g., during rotation of the coil on a support, during a following binding of the coil with a binding material, and during subsequent transportation of the coil.

In addition, the spaced strip beginning 20 holds another dangerous potential because the spaced strip holds a danger of injury for personnel.

Correspondingly, with the method shown in FIGS. 5 and 6, the strip beginning 20 is deflected with such a small force f that actually only an elastic deformation takes place and not a plastic deformation, the contribution of the method consisting in that the quality of the coil material is improved, and the difficulties during handling are reduced.

Figure 7:
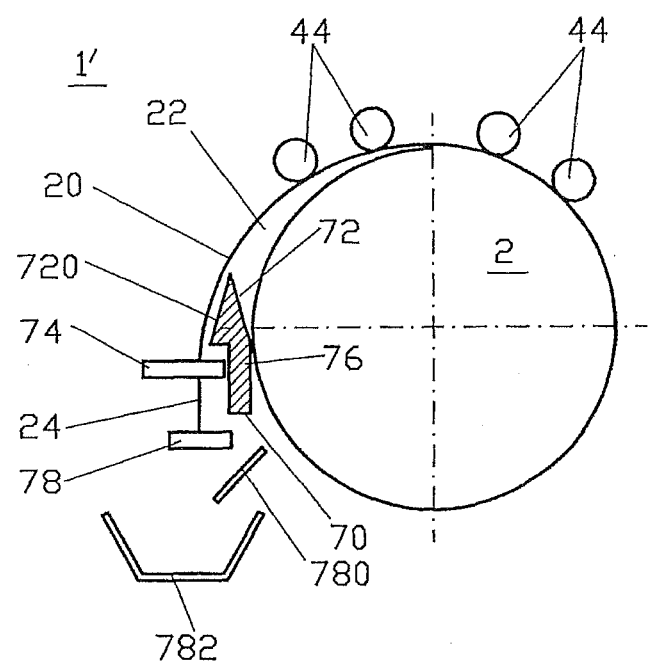
FIG. 7 a schematic view illustrating of another device for removing samples.

FIG. 7 shows schematically a device for removing samples from coil 2. Here again, the contact rolls 44 are shown schematically and serve for preventing springing up of the coil after loosening of the binding. The coil 2 typically are arranged on the bottom roll units, not shown in FIG. 7.

The strip beginning 20 is pulled off the coil 2 as a result of translational and/or rotational movement of the coil so that the strip beginning 20 moves away from the coil. This away-movement is supported by a deflection device 70 that includes a wedge-shaped deflection element 72. The wedge-shaped deflection element 72 is so positioned and aligned and is so geometrically formed that the force that the deflection element 72 applies to the strip beginning 20, is so small that a remaining plastic deformation is not reached in the strip beginning 20, only an elastic deflection takes place. The deflection device 70, which is shown in FIG. 7, is essentially wedge-shaped with a sharp angle. Other geometrical forms can also be contemplated as long as they provide for an elastic deformation.

The deflection element 72 is essentially moved tangentially toward the outer surface of the coil 2 so that a simple lift-off of the strip beginning 20 from the beneath located layer 22 of the coil 2 is achieved.

The respective guide surfaces 720 of the deflection element 72 are so formed that the strip beginning 20 is lifted off the below located layer 22 while the resulting angle and the applied force do not lead to a remaining plastic deformation.

In order to be able to remove a sample from the strip beginning or to simply clear the strip beginning, a separation device is provided which is shown in form of a cutting knife that operates against an outer surface 76 of the deflection device 70. The separation device acts on the strip beginning in a direction essentially transverse to the below located layer 22 of the coil.

The outer surface 76 of the deflection device 70 can, however, be formed as a protection surface, as a guide or as another element that enables the separation of the sample 24 from the strip beginning 20 by thermal or mechanical cutters or by a machining method.

There is also provided a stop 78 against which the strip beginning 20 is supported before the separation device 74 removes the sample 24.

A material guiding system 780 and a material collection system 782 are likewise provided for guiding and collecting the separated samples 24 in order to be able to transport them for a following analysis.

The maximum allowable elastic deformation of the material and the following therefrom geometry of the deflection device 70 can be determined beforehand, e.g., by calculation, practical experimentation, and based on the empirical data.

The relative movement of the coil 2 relative to the deflection device 70 can be achieved either by rotating the coil 2 on a support such as, e.g., bottom rollers or by moving the deflection device 70 relative to a stationary coil 2.

The geometry of the deflection element 72 or its alignment or adjustment with respect to the coil insures that the applied deflection force is a simple elastic force.

The unwinding of the material beginning can be monitored by direct or indirect measuring sensors which monitor the strip beginning 20 and, correspondingly, the deformation of the strip beginning can be so calculated that only an elastic deformation takes place.

The stop 78 can be adjustable relative to the separation device 74 to enable separation of sample with different dimensions.

By following the strip beginning 20 in combination with a suitable calculation method, the deviation from the preliminary calculated or determined deformation values can be recognized, and the deviation can be used for influencing the relative movement of the coil 2 and the deflection device 70 and the positioning of the stop 78.

The cutting device 74 can be so formed that it can be adapted to different parameters of the material of coil 2, e.g., to strip thickness, strip width, to the material composition, and its flatness.

In addition to the outer surface 76, the deflection device 70 can be provided with other protection elements, e.g., a screening sheet or the like for protecting the below located layer 22 of the coil during separation of the sample.

LIST OF REFERENCE NUMERALS 1,11 Device for removing samples
2 Coil
20 Strip beginning
30 Stationary bottom roll unit
32 Movable bottom roll unit
34 Rolls of the bottom roll units
36 Displacement device
302 Guide device for strip binding material
322 Guide device for strip binding material
40 First contact roll unit
42 Second contact roll unit
44 Rolls of the contact roll units
46 Displacement device
48 Adjusting device
402 Folding guide device for strip binding material
404 Guide device for strip binding material
5 Sample removing station
50 Sample removing station
60 Strip binding device
62 Gate
64 Strip binding material
66 Strip connection device
70 Deflection device
72 Deflection element
74 Separation device
76 Outer surface
78 Stop
720 Guide surface
780 Material guide system
782 Material collection system

The invention claimed is:

1. A device (1) for removing a sample (24) from a coil (2), comprising first and second bottom roll units (30, 32) for supporting the coil (2) during removal of the sample; first and second contact units (40, 42) associated, respectively, with the first and second bottom units (30, 32) and pressable against an outer surface of the coil (2); and a binding device for binding the coil (2) supported on the first and second bottom units, wherein the first and second bottom roll units (30, 32) are circumferentially offset relative to each other by 90° with respect to center of the coil, and the first and second contact units (40, 42) are circumferentially offset, with respect to the center of the coil, respectively, relative to the first and second bottom units (30,32) also by 90°.

2. A device according to claim 1, wherein the first and second bottom roll units (30, 32) and the first and second contact units (40, 42) each is provided with a guide device for guiding a strip binding material around the coil.

3. A device according to claim 1, wherein rolls (34) of the bottom roll units (30, 32) and/or rolls (44) of the contact roll units (40, 42) have, respectively, at least two roll units so that a strip binding material (64) is displaceable therethrough and/or a strip binding channel is formed therebetween.

4. A device according to claim 1, first and second bottom roll units is stationary, and another of the wherein one of the first and second bottom roll units is displaceable.

5. A device according to claim 1, wherein a sample removing device (5) for removing a sample (24) from a strip beginning (20) of the coil (2) is provided.

6. A device according to claim 1, comprising a deflection device (70) for deflecting a material beginning (20) of the coil (2) from a beneath located layer (22), wherein the deflection device is so formed that the strip beginning of the coil (2) only elastically deflected from the beneath located layer (22).

7. A device according to claim 6, wherein the deflection device (70) has a deflection element (72) that has such a geometry, alignment, and/or setting that a strip beginning (20) of the coil (2) is so deflected with a force (f) from the beneath located layer (22) that simply an elastic deformation of the strip beginning (20) takes place.

8. A device according to claim 7, wherein the deflection element (72) is formed as a wedge with an acute angle.

9. A device according to claim 6, wherein the deflection device (70) is advanced to an outer surface of the coil (2) substantially tangentially and a deflection element (72) is advanced to the outer surface of the coil (2).

10. A device according to claim 6, wherein a separation device (74) for separating a sample (24) from the coil (2) is provided, wherein the separation device acts on the strip beginning transverse to the beneath located layer of the coil.

11. A method of removing a sample of a coil (2), comprising the steps of:
providing a device (1) for removing a sample (24) from a coil (2), and comprising first and second bottom roll units (30, 32) for supporting the coil (2) during removal of the sample; first and second contact units (40, 42) associated, respectively, with the first and second bottom units (30, 32) and pressable against an outer surface of the coil (2); and a binding device for binding the coil (2) supported on the first and second bottom units, wherein the first and second bottom roll units (30, 32) are circumferentially offset relative to each other by 90° with respect to center of the coil, and the first and second contact units (40, 42) are circumferentially offset, with respect to the center of the coil respectively, relative to the first and second bottom units (30,32) also by 90°;
positioning of the coil (2) on the first and second bottom roll units (30, 32);
pressing the first and second contact units (40, 42) which are associated with the first and second bottom roll units against an outer surface of the coil (2).

12. A method according to claim 11, wherein binding the coil (2) supported on the first and second bottom roll units (30, 32) with a binding device that advances a strip binding material through guide devices provided on each of the first and second bottom roll units and first and second contact units for binding the coil.

* * * * *